(12) United States Patent
Narayanan et al.

(10) Patent No.: US 6,723,373 B1
(45) Date of Patent: Apr. 20, 2004

(54) DEVICE AND PROCESS FOR COATING STENTS

(75) Inventors: Pallassana Narayanan, Belle Mead, NJ (US); Gerard H. Llanos, Stewartsville, NJ (US); David Cook, Oakville (CA); Jacob Leidner, Toronto (CA)

(73) Assignee: Cordis Corporation, Miami Lakes, FL (US)

( * ) Notice: Subject to any disclaimer, the term of this patent is extended or adjusted under 35 U.S.C. 154(b) by 13 days.

(21) Appl. No.: 09/595,876

(22) Filed: Jun. 16, 2000

(51) Int. Cl.[7] .................................................. B05D 3/00
(52) U.S. Cl. ..................... 427/2.25; 427/2.24; 623/1.46
(58) Field of Search ................. 623/1.42, 1.46; 604/96; 606/191, 194, 195, 198; 427/2.25, 2.3, 2.24

(56) References Cited

U.S. PATENT DOCUMENTS

| | | | | |
|---|---|---|---|---|
| 4,474,630 A | * | 10/1984 | Planck et al. | 156/62.4 |
| 5,229,045 A | * | 7/1993 | Soldani | 264/41 |
| 5,449,382 A | * | 9/1995 | Dayton | 623/1.46 |
| 5,605,696 A | * | 2/1997 | Eury et al. | 424/423 |
| 5,624,411 A | * | 4/1997 | Tuch | 604/265 |
| 5,837,313 A | * | 11/1998 | Ding et al. | 427/2.21 |
| 5,897,911 A | * | 4/1999 | Loeffler | 427/2.25 |
| 6,056,993 A | * | 5/2000 | Leidner et al. | 427/2.25 |
| 6,153,252 A | * | 11/2000 | Hossainy et al. | 427/2.3 |
| 6,203,551 B1 | * | 3/2001 | Wu | 606/108 |
| 6,273,913 B1 | * | 8/2001 | Wright et al. | 623/1.42 |
| 6,517,889 B1 | * | 2/2003 | Jayaraman | 427/2.24 |
| 2003/0215564 A1 | * | 11/2003 | Heller et al. | 427/2.25 |

FOREIGN PATENT DOCUMENTS

EP     0 850 651 A2 * 1/1998 ............ A61I/27/00

* cited by examiner

*Primary Examiner*—David H. Willse
*Assistant Examiner*—Javier G. Blanco
(74) *Attorney, Agent, or Firm*—Paul A. Coletti

(57) ABSTRACT

A stent is positioned on an undersized mandrel and the stent is coated with an excess of a polymer and drug solution. The stent is rotated to spin off the excess of the coating. The stent is then moved into a new, clean position on the mandrel. The process is repeated a few times, after which time the coating is already dry and non-sticky. This process forms a conforming coating. Various important polymer solution parameters include viscosity, solvent evaporation rate and several others. The actual type of coating polymer is not as important as how the surface of the stent is treated, according to the steps described herein.

12 Claims, 22 Drawing Sheets

100μm x 100

1mm x 25

1mm x 35

10μm x 500

10μm x 500

10μm x 500

1mm x 30

10μm x 600

1mm x 30

1mm x 30

10μm x 600

1mm x 20

100μm x 100

100μm x 100

1mm x 20

100μm x 100

1mm x 20

100μm x 75

1mm x 20

100μm x 75

DEVICE AND PROCESS FOR COATING STENTS

FIELD OF THE INVENTION

This invention relates to coating of stents. These stents contain a medicated coating composed of an immunosuppressing drug dispersed in a polymer matrix. The purpose of the coating (about 10 to 15 μm thick) is to slowly release medication that will inhibit the proliferation of smooth cells and therefore reduce risk of restenosis.

BACKGROUND OF THE INVENTION

Three elements are required for a successful coating of a stent—the resin, the drug, and the application process. There have been identified a number of generic classes of materials, which can be considered as possible binders for the coating formulation. A process for applying these coatings in a reproducible fashion is required in order to evaluate the coatings. This invention deals with the development of such a process. Processes for coating stents are described, for instance, in Ser. No. 09/061,568, filed Apr. 16, 1998, and Ser. No. 09/512,432 filed Feb. 25, 2000, both of which are assigned to a common assignee and are incorporated herein by reference.

Thus, the objective of this invention is to produce a thin (around 10 μm) conformal coating of polymer containing drug on the struts of the stent. The coating should encapsulate the struts of the stent so that the danger of small pieces of coating lifting or breaking off is eliminated. At the same time the coating had to be applied in such a way so as not to fill the openings between the struts or in any way obstruct the mechanical performance of the stent.

SUMMARY OF THE INVENTION

In summary, a stent is positioned on an undersized mandrel and the stent is coated with an excess of a polymer and drug solution. The stent is rotated to spin off the excess of the coating. The stent is then moved into a new, clean position on the mandrel. This forward movement is believed to remove excess solution from the inside of the stent. The process is repeated a few times, after which time the coating is already dry and non-sticky. This process forms a conformal coating. It should be understood that in terms of the process, important polymer solution parameters include viscosity, solvent evaporation rate and several others. The actual type of coating polymer is not as important as how the surface of the stent is treated, according to the steps described herein.

According to the present invention, the following steps are followed for coating a drug to a stent.
1. The stents are cleaned in a beaker to which about 20 ml solvent is added.
2. Cover with a watch glass.
3. Sonicate the stent/solvent beaker for about 1 minute.
4. Leave stents in solvent until use.
5. Clean 1.27 mm diameter mandrel by wiping with acetone. Set aside to dry on a clean surface.
6. Place stent on mandrel by using end of mandrel to insert into one end of the stent and slowly pushing onto the mandrel from the solution.
7. By tapping the mandrel from the opposite end, allow the stent to slide over the mandrel to the opposite end of the mandrel. One can also use a scalpel to slowly push the stent down; it should move freely.
8. Insert mandrel into mandrel chuck on apparatus (see FIG. 22)
9. Once on the apparatus, turn on the mandrel motor and rotate at high speed for a few seconds while blowing the stent with dry, clean nitrogen gas. This serves to dry the stent from any residual solvent
10. Weigh out a silicone polymer solution into a vial.
11. Weigh out the (rapamycin) drug and put into vial.
12. Add solvent (e.g. xylene) to vial. Record weights of all components.
13. Seal the vial with a screw top (note: vial top should be compatible with the solvents in use) and then shake the vial to mix the components. Sonicate the mixture for about 5 minutes.
14. Using a plastic syringe, transfer a small amount (about 0.5 ml) of the solution onto the stent by dropping the solution over the stent on the mandrel, thoroughly coating the stent.
15. Immediately turn on the mandrel motor and rotate at about 4000 RPM. This serves to throw off any excess solution from the stent and provide the proper distribution of the solution on the stent surface. Turn the motor on and off in pulses of about 1 second. This process serves to constantly accelerate/decelerate the stent to keep the stent moving relative to the mandrel so that it avoids sticking to the mandrel.
16. After about 15 seconds, turn off the motor and move the stent about one stent length along the mandrel to a clean section. Run the mandrel motor and pulse the motor for about 10 seconds. Repeat this step two (or more) times.
17. Turn off the motor and move the stent about 2 stent lengths down the mandrel to a clean section. Turn on the motor and run it at full speed while blowing the stent with clean, dry nitrogen for a time of about 20 seconds.
18. Turn off the motor; slowly move the stent forward to push it off the mandrel into a receiving vial.
19. Remove the mandrel from the apparatus, clean, and prepare for the next run.
20. A preferred polymer is an RTV (room temperature vulcanization, i.e., curing) silicone, which means that it cures at room temperature in about 24 hours. Moisture is required for the cure. Therefore, place the stent in a very moist environment. One easy way to do this is to use a forced air oven and place a container of water at the bottom of the oven. Maintain the oven temperature at ambient or slightly above. The forced air absorbs the moisture by evaporation from the container and cures the polymer on the stent.

DESCRIPTION OF THE DRAWINGS

The present invention will be better understood in conjunction with the following drawings, in which.

DETAILED DESCRIPTION OF THE INVENTION

For this invention, there has been suggested the following drug/polymer combination for the stent coating:

Drug: "rapamycin", $C_{51}H_{79}NO_{13}$, an immunosuppressant

Polymer: MED3-6605 RTV silicone, supplied as a 20% solution in 1,1,1-trichloroethane solvent, from NuSil Silicone Technology, Carpinteria, Calif. 93013.

The stent to be coated were PS153 model stents (Cordis Corporation, Miami Lakes Fla.) and the rapamycin drug. The MED3-6605 solution and SP-1 silicone adhesion primer were acquired from NuSil.

In this project, it was desired to focus on dip coating methods, as opposed to spraying. Two approaches were considered:

Dip and dry—dip the stent in the coating solution, let the solution drain and then dry to form coat;

Coat, move on a mandrel and dry—dip stent in coating solution, move onto a mandrel, push along the mandrel to remove excess coating solution and then dry to form coat.

It was subsequently found that the "dip and dry" method did not work well, as the solution dried too quickly leaving a blob of silicone on the stent. Thereafter the coating method was focused upon.

EXAMPLE 1

Stent mandrels were prepared from long septum needles (Popper & Sons, Inc.) with outside diameters of 0.7 mm (22 gauge), 1.05 mm (19 gauge), 1.27 mm (18 gauge) and 1.48 mm (17 gauge). Septum needles have hardened, smooth surfaces which are particularly suitable for use in this application. The needles were cut from a luer syringe attachment and the ends were polished to remove any sharp edges.

A stent was coated using the following procedure:

Dip stent into MED3-6605 solution, then transfer to 0.9 mm diameter mandrel. Shake off the excess solution and move forward on mandrel, dry, and push off into collection vial (Procedure A).

| Stent # | Solution Used | Coating Procedure | Observations |
| --- | --- | --- | --- |
| 99-05-8071-05-1 | MED3-6605 | A | Coating much too thick, covered all openings |

Figure 1:
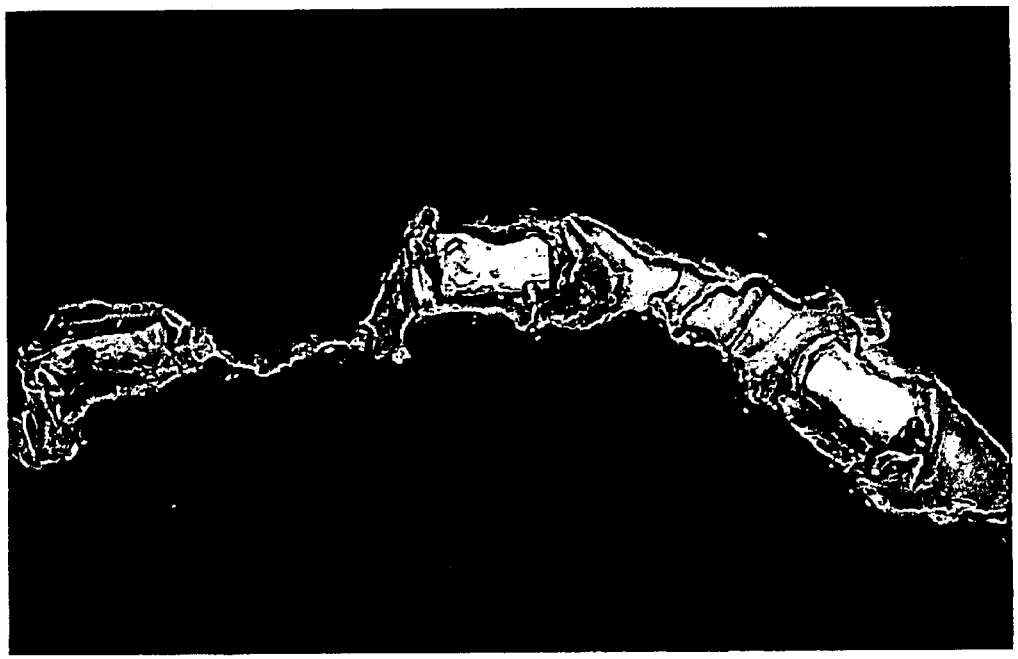
FIGS. 1–20 are scanning electron micrographs (SEMs) of stents coated according to the examples described herein.

Again, it was found that that the polymer solution dried too quickly. Using scanning electron micrography ("SEM"), the coating was found to be much too thick (see FIG. 1).

EXAMPLE 2

It was apparent from the previous trials that the NuSil MED3-6605 20% silicone solution was too viscous to obtain the desired 10 to 15 μm layer coating thickness. Therefore, dilution was necessary.

To dilute the solution, ethyl acetate solvent (Omnisolv, BDH, Toronto, Ontario spectroscopic grade) was used. This solvent was chosen based on previous experience with this type of silicone solution in a spray coating application. It has comparable solvency for silicones and has a boiling point and evaporation rate similar to 1,1,1-trichloroethane. Solutions of 9.8%, 5.1%, and 2.3% silicone were prepared as shown below:

| Solution # | % Silicone | Added Solvent | Total % Solids |
| --- | --- | --- | --- |
| 99-05-8071-04-2 | 9.76 | ethyl acetate | 9.76 |
| 99-05-8071-04-3 | 5.10 | ethyl acetate | 5.10 |
| 99-05-8071-04-4 | 2.29 | ethyl acetate | 2.29 |

The previous experiment also indicated that too much solution remained even after shaking to remove the excess. Therefore, the method was changed to include a rotational spin, which removed the excess solution, by centrifugal force (Procedure B). The stents coated using this procedure are shown below:

| Stent # | Solution Used | Coating Procedure | Observations |
| --- | --- | --- | --- |
| 99-05-8071-05-2 | 99-05-8071-04-2 | B | Many blocked openings (see FIG. 2) |
| 99-05-8071-05-3 | 99-05-8071-04-3 | B | Some blocked openings |
| 99-05-8071-05-4 | 99-05-8071-04-4 | B | Very thin coating (see FIGS. 3 & 4) |

Figure 2:
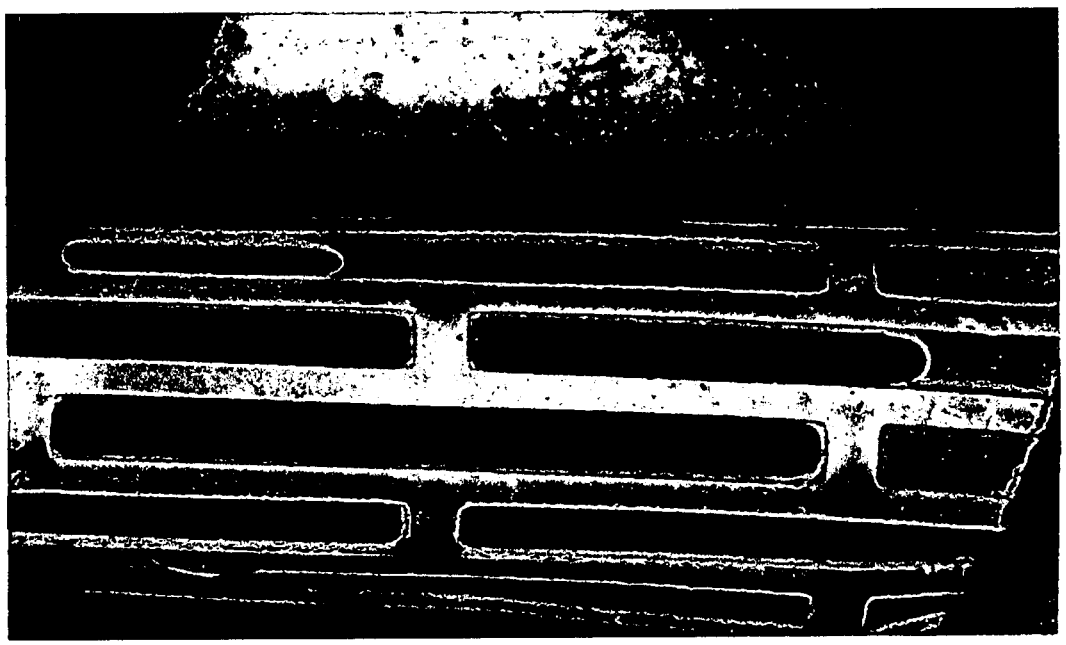
Figure 3:
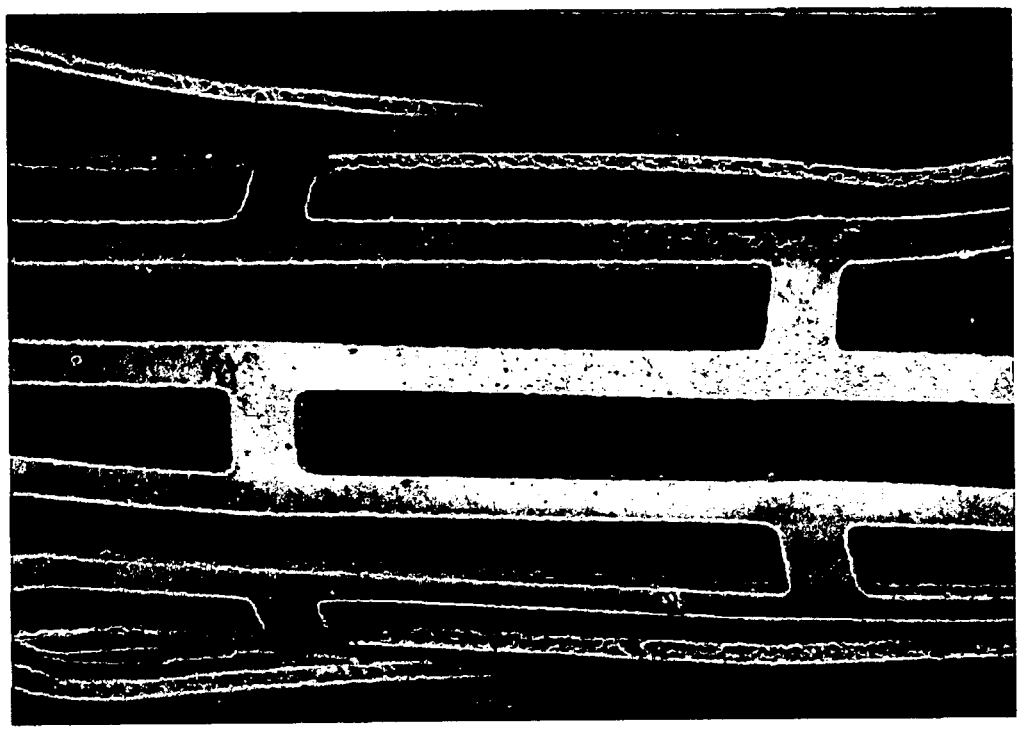
Figure 4:

Visual examination of the coated stents showed that all had blockage of at least some of the stent openings (see FIG. 2). The most dilute coating had minimal blockage, but the coating thickness was relatively thin (<1 μm) (FIGS. 3 and 4). Nevertheless, it was apparent that this method held the most promise for further development.

From the foregoing, it was suspected that the solvent evaporation rate would have a significant effect on the coating procedure. To test this theory, two solvents were used in place of ethyl acetate—toluene (Fisher Scientific, Toronto, Ontario, certified ACS grade) and diethyl ether (Fisher Scientific, Toronto, Ontario, certified ACS grade). Toluene has an evaporation rate roughly ⅓ that of trichloroethane, whereas diethyl ether is about 3 times faster.

EXAMPLE 3

It was decided to position the stent on a 0.9 mm mandrel close to one end. Thereafter, solution was applied to the stent, rotated with fingers. The mandrel was shaken to remove excess solution. Slowly move stent forward on mandrel towards far end, drying as the stent moves forward. Push off into collection vial and let cure overnight at ambient conditions. (This was Procedure C.)

Solutions were made up as shown below starting with a 10% solid mixture:

| Solution # | % Silicone | Added Solvent | Total % Solids |
| --- | --- | --- | --- |
| 99-05-8071-08-1 | 10.00 | toluene | 10.00 |
| 99-05-8071-08-2 | 4.99 | toluene | 4.99 |
| 99-05-8071-08-3 | 2.62 | toluene | 2.62 |
| 99-05-8071-08-4 | 10.65 | diethyl ether | 10.65 |
| 99-05-8071-08-5 | 5.48 | diethyl ether | 5.48 |
| 99-05-8071-08-6 | 3.52 | diethyl ether | 3.52 |

The solutions were used to prepare the stents as shown below with coating procedures as listed.

| Stent # | Solution Used | Coating Procedure | Observations |
| --- | --- | --- | --- |
| 99-05-8071-10-1 | 99-05-8071-08-1 | C | Some bridged openings |
| 99-05-8071-10-2 | 99-05-8071-08-2 | C | Some bridged openings |
| 99-05-8071-10-3 | 99-05-8071-08-3 | C | Very thin coating |
| 99-05-8071-10-4 | 99-05-8071-08-4 | C | Thick coating, blockage of openings |
| 99-05-8071-10-5 | 99-05-8071-08-5 | C | Blockage of openings |
| 99-05-8071-10-6 | 99-05-8071-08-6 | C | Blockage of openings |

It was found that the diethyl ether solutions evaporated too quickly and coatings were poorly formed on the stents, whereas the toluene solvent gave much more evenly coated stents. Still, problems with blockage of stent openings remained.

It had previously been noted that that a relatively close-fitting mandrel gave the best coating results. In lieu of this and taking into consideration the above results, the following changes were made. We decided to use of a 1.5 mm mandrel and the solvent xylene (Fisher Scientific, certified ACS grade) solvent, which has even a lower evaporation rate than toluene.

EXAMPLE 4

Solutions of about 10% solids content were made as shown below:

| Solution # | % Silicone | Solvent | Total % Solids |
|---|---|---|---|
| 99-05-8071-26-1 | 10.28 | Xylene | 10.28 |
| 99-05-8071-26-2 | 11.18 | Xylene | 11.18 |
| 99-05-8071-26-3 | 12.50 | Xylene | 12.50 |

The solutions were used to prepare the stents as shown below using coating procedures as listed:

| Stent # | Solution Used | Coating Procedure | Observations |
|---|---|---|---|
| 99-05-8071-27-1 | 99-05-8071-26-1 | C | Some blockage |
| 99-05-8071-27-2 | 99-05-8071-26-2 | C | Some blockage |
| 99-05-8071-28-1 | 99-05-8071-26-3 | C | Some blockage |
| 99-05-8071-29-1 | 99-05-8071-26-3 | D | Some blockage |

Note: for procedure D, we used NuSil SP-120 coating on stents prior to placing the stents on mandrel, and thereafter followed the steps of procedure C.

Figure 5:
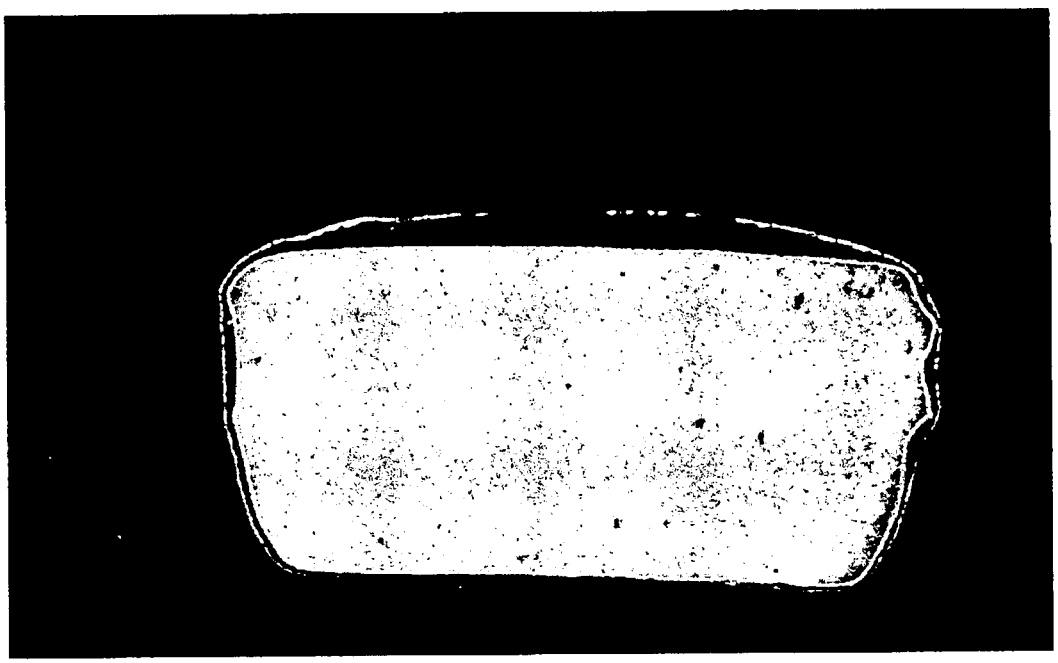

It was found that the close fitting mandrel did reduce the amount of stent opening blockage and that the coating seemed more uniform on the stents (see FIG. 5). However, it was difficult to remove the stent without damaging it as it essentially was bonded to the mandrel by the coating. Examination under a microscope also showed that coating material "piled up" at one end of the stent openings as the stent was pushed forward along the mandrel.

Silicone alone had been used in previous experiments, but in this series of experiments, a drug (rapamycin) was added.

EXAMPLE 5

For this series of runs the diameter of the mandrel was varied along with details of the preparation method, while only one coating solution was used as shown below:

| Solution Number | % Silicone | Solvent | % Rapamycin | Total % Solids | % Rapamycin in Solids |
|---|---|---|---|---|---|
| 99-05-8071-32 | 8.73 | Xylene | 2.82 | 11.55 | 24.40 |

This solution was used to prepare the stents as shown below using coating procedures as listed:

| Stent # | Solution Used | Coating Procedure |
|---|---|---|
| 99-05-8071-33 | 99-05-8071-32 | F |
| 99-05-8071-34-1 | 99-05-8071-32 | G |
| 99-05-8071-34-2 | 99-05-8071-32 | H |
| 99-05-8071-34-3 | 99-05-8071-32 | I |
| 99-05-8071-34-4 | 99-05-8071-32 | J |
| 99-05-8071-34-5 | 99-05-8071-32 | K |

Procedure F: The stents were cleaned by sonication in dichloromethane (DCM) for 1 minute. This removed any dirt or fibers adhering to the stent. The stents were left in the DCM solvent until use. A stent was placed on a 1.55 mm diameter mandrel and the mandrel was spun rapidly between the fingers for about 20 seconds to remove DCM. The stent was dried under a stream of dry nitrogen gas. The coating solution was delivered to the stent using a 1.0 ml syringe. The mandrel was spun rapidly for about 10 seconds to remove excess solution. The stent was pushed forward on the mandrel at least one stent length and the spinning operation repeated for another 10 seconds. The stent was moved forward again on the mandrel, rotated, and dried with nitrogen gas.

Procedure G: This was the same as Procedure F, except to spin the 1.55 mm mandrel between the fingers for 20 seconds.

Procedure H: This was the same as Procedure G, except spin for 1 minute.

Procedure I: This was the same as Procedure G, except to use a 1.27 mm mandrel and to spin for 20 seconds.

Procedure J: This was the same as Procedure G, except to spin for 10 seconds on a 0.9 mm mandrel.

Procedure K: This was the same as Procedure J, except to spin for 30 seconds.

Figure 6:
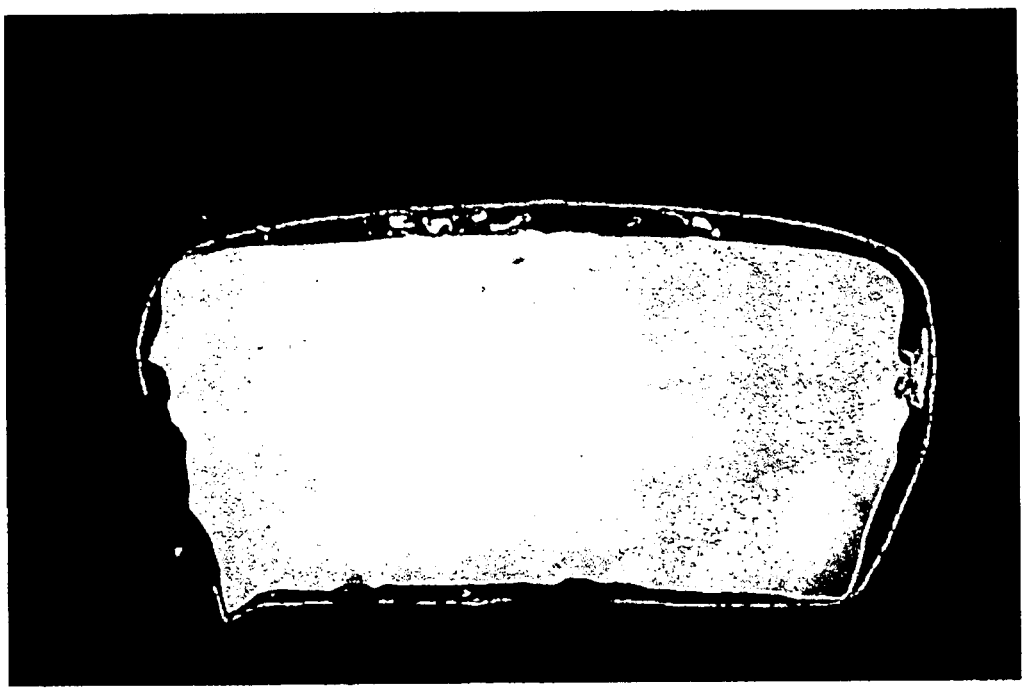

From these experiments it was found that the 1.27 mm diameter mandrel gave very good results (see FIG. 6), as the coating material did not "bunch up" at the end of the openings as with the 1.5 mm mandrel experiments. Conversely, the coating was too thick and of poor quality with the 0.9 mm diameter mandrel.

Overall, long spin times had no observable effect on the coating quality; about 20 seconds was deemed sufficient.

The Coating Apparatus

Figure 21:
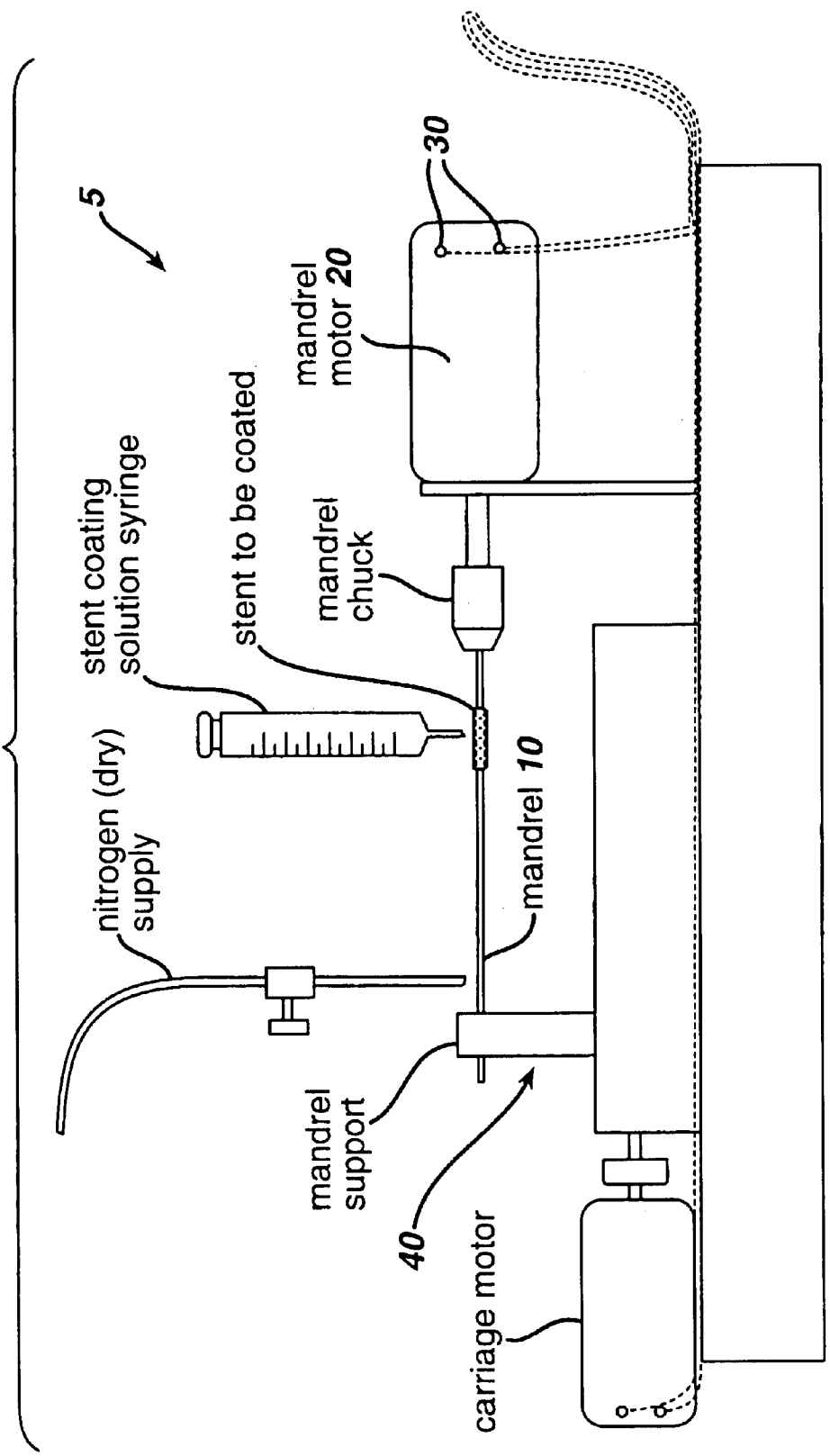
FIGS. 21 and 22 are schematics of a device used in the current process.

An apparatus 5 (see FIG. 21) was assembled to mechanize some of the steps derived from the previous experience to improve the reproducibility of the coating procedure. The setup consists of a mandrel 10 driven by a high-speed motor 20 with momentary switches 30 and a movable stage 40 for bearing support of the mandrel 10 during the coating operation.

EXAMPLE 6

Rapamycin and silicone-only solutions were prepared as listed below:

| Solution Number | % Silicone | Solvent | % Rapamycin | Total % Solids | % Rapamycin in Solids |
|---|---|---|---|---|---|
| 99-05-8071-40-1 | 9.47 | Xylene | 4.32 | 13.80 | 31.3 |
| 99-05-8071-40-2 | 13.69 | Xylene | 0 | 13.69 | 0 |

The stents [Palmaz—Schatz® Crown stents Cordis, Miami Lakes Fla.) were prepared using the solutions listed below:

| Stent # | Solution Used | Coating Procedure |
|---|---|---|
| 99-05-8071-41-1 | 99-05-8071-40-1 | L |
| 99-05-8071-41-2 | 99-05-8071-40-1 | M |
| 99-05-8071-42-1 | 99-05-8071-40-1 | L |
| 99-05-8071-42-2 | 99-05-8071-40-1 | L |
| 99-05-8071-42-3 | 99-05-8071-40-1 | N |
| 99-05-8071-43-1 | 99-05-8071-40-1 | O |
| 99-05-8071-43-2 | 99-05-8071-40-2 | P |

Procedure L: First, clean stents using sonication for one minute in DCM. Insert a stent on a 1.27 mm diameter mandrel and dry with nitrogen gas. Fix the mandrel 10 into the apparatus and coat stent with solution. Immediately spin at 2500 RPM for about 5 seconds. Move the stent forward at least one stent length and repeat the spin procedure. Move the mandrel forward one additional stent length and spin. If stent moves freely on mandrel, dry with a nitrogen gas flow for about 10 seconds and then transfer stent from mandrel into glass vial.

Procedure M: This was the same as Procedure L, except to spin the mandrel at 1200 RPM for 5 seconds.

Procedure N: This was the same as Procedure L, except to spin the mandrel at 2500 RPM for 10 seconds, using a 1.50 mm mandrel.

Procedure O: This was the same as Procedure L, except to spin the mandrel at 4000 RPM for 15 seconds.

Procedure P: This was the same as Procedure L, except to spin the mandrel at 4000 RPM for 30 seconds.

It was found that the apparatus significantly improved the problem of slot clogging of the coating on the stents. More than likely, this was attributed to the higher speeds "flinging away" excess solution at the very beginning of the coating process. It was observed that the best procedure was that with 4000-RPM spin for 15 to 30 seconds.

Figure 22:
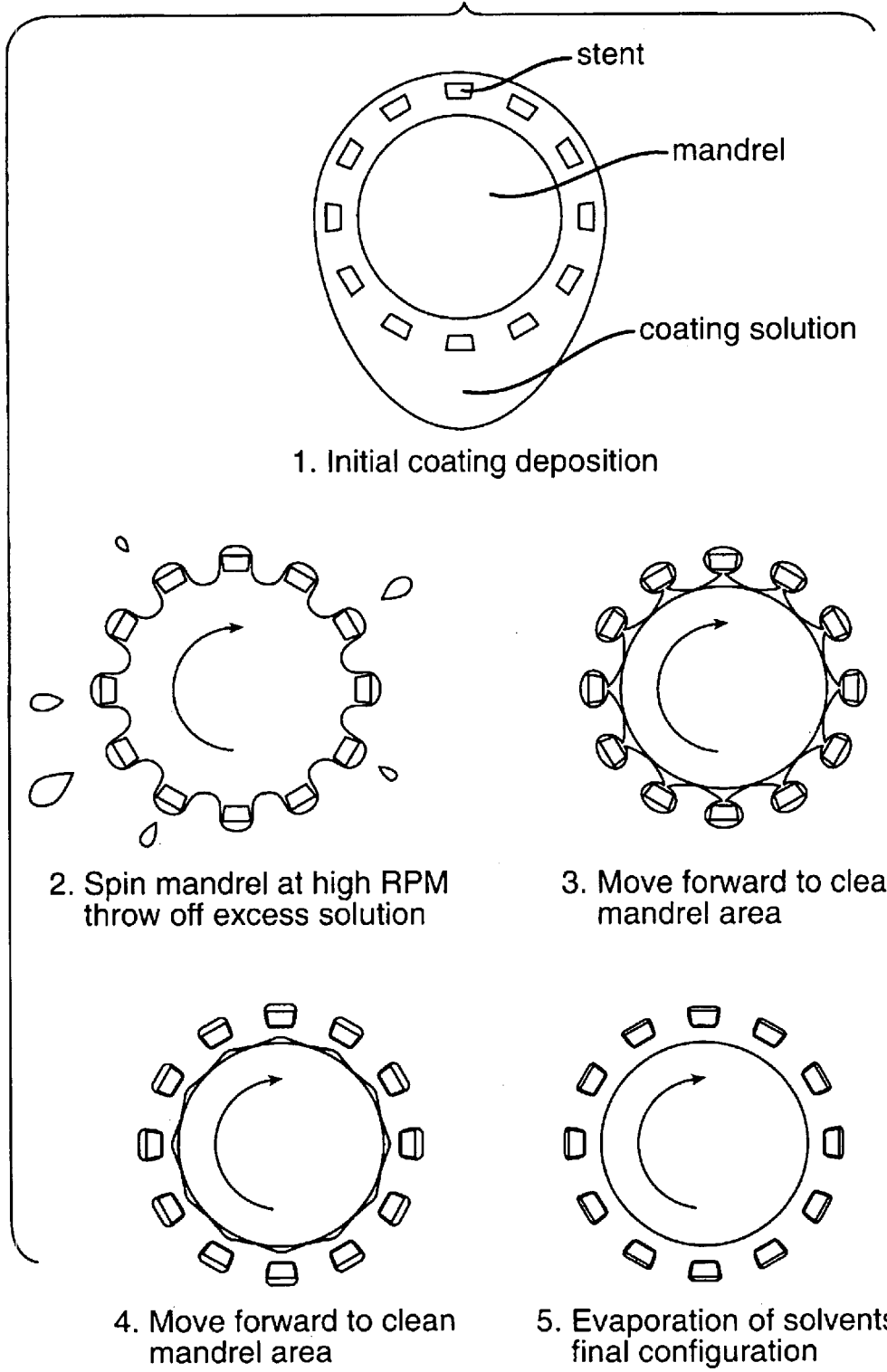

A model of the coating process is shown in FIG. 22. In step 1 the stent is covered (in excess) with the coating solution. As the mandrel 10 and stent 100 are brought up to high revolutions, excess solution is thrown away from the stent on its outer side, although more solution is retained in the stent/mandrel gap 25 (step 2). However, as the stent 100 is moved forward (using carriage motor 20) on the mandrel the inner coating solution is left behind on the mandrel 10. Eventually the stent 100 is no longer in contact with the solution on its underside, while contacting the mandrel 10. (Steps 3 & 4.) Finally, the wet solution remaining only on the stent 100 is dried with applied nitrogen gas (step 5).

EXAMPLE 7

Coated Stent Evaluation

For evaluation purposes, a series of rapamycin/silicone-coated and silicone-only stents were prepared. The solutions used for the coating preparation are shown below:

| Solution Number | % Silicone | Solvent | % Rapamycin | Total % Solids | % Rapamycin in Solids |
|---|---|---|---|---|---|
| 99-05-8071-64-1 | 11.05 | Xylene | 3.61 | 14.66 | 24.61 |
| 99-05-8071-67-7 | 13.32 | Xylene | 0 | 13.32 | 0 |

Again, the stents were Palmaz Schatz® Crown stents of varying lengths as described below. Eight each of rapamycin/silicone and silicone-only coated stents were prepared:

| Silicone Coated Stent # | Silicone/Rapamycin Coated Stent # |
|---|---|
| 99-05-8071-67-8 | 99-05-8071-66-5 |
| 99-05-8071-67-9 | 99-05-8071-66-6 |
| 99-05-8071-67-10 | 99-05-8071-67-1 |
| 99-05-8071-67-11 | 99-05-8071-67-2 |
| 99-05-8071-67-12 | 99-05-8071-67-3 |
| 99-05-8071-67-13 | 99-05-8071-67-4 |
| 99-05-8071-68-2* | 99-05-8071-67-5* |
| 99-05-8071-68-3* | 99-05-8071-67-6* |

The stents marked with an asterisk (*) on the chart above were also pre-coated with SP1 silicone adhesion primer (Manufacturer: NuSil).

Figure 7:
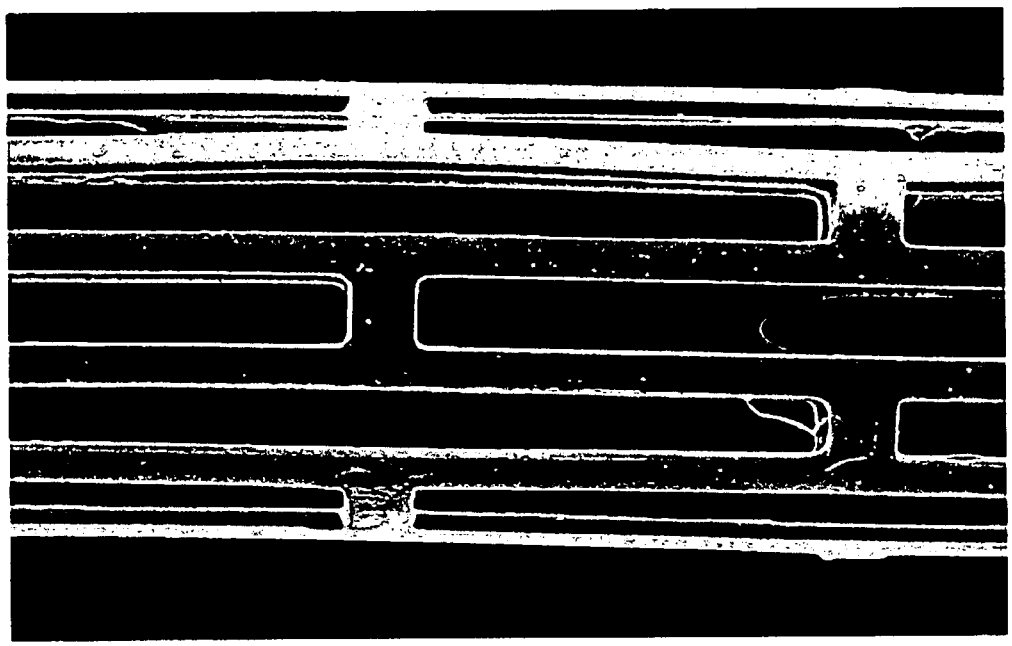
Figure 8:
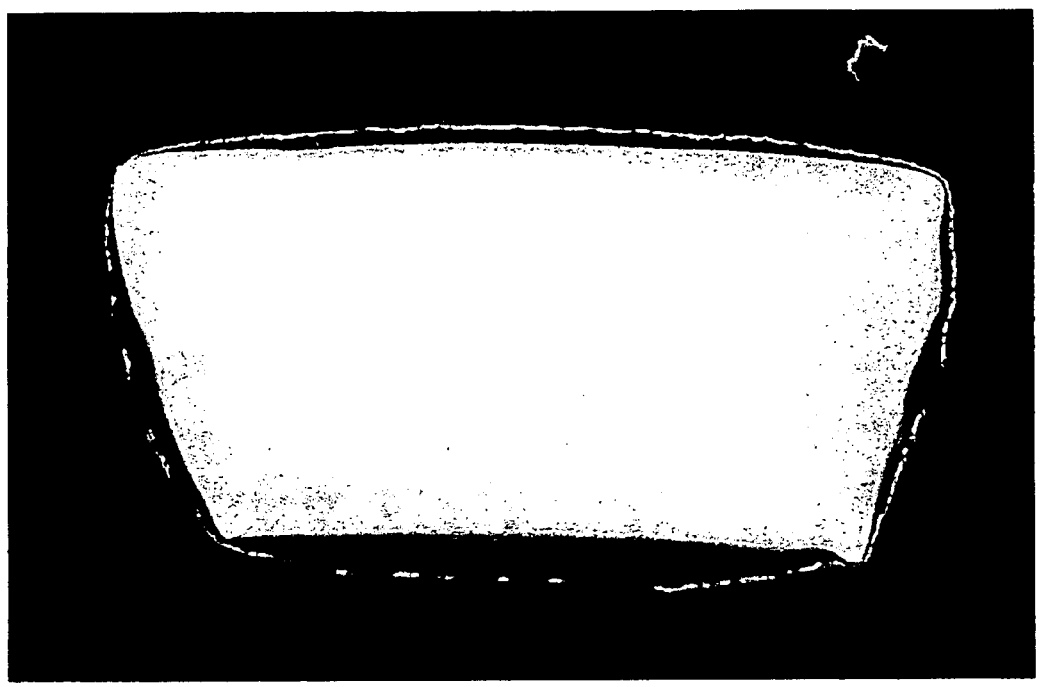

A scanning electron micrograph of a typical silicone-only stent surface is seen in FIG. 7 (for 99-05-8071-67-10) which shows a fairly smooth, even coating. The thickness for the coat (see FIG. 8) is somewhat thin at about 3 $\mu$m to 10 $\mu$m.

Figure 9:
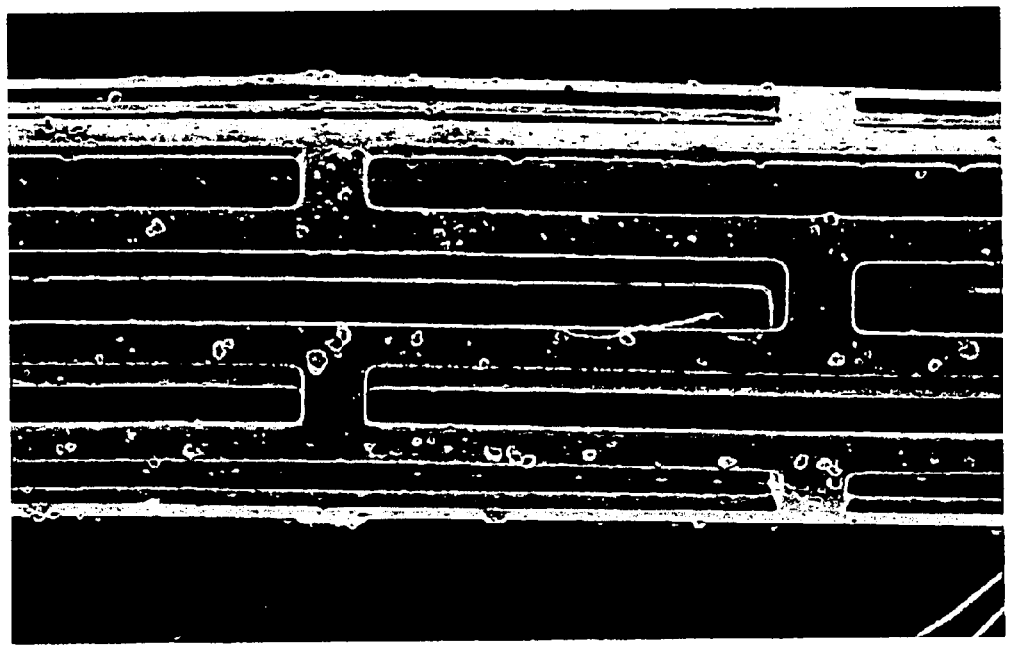
Figure 10:
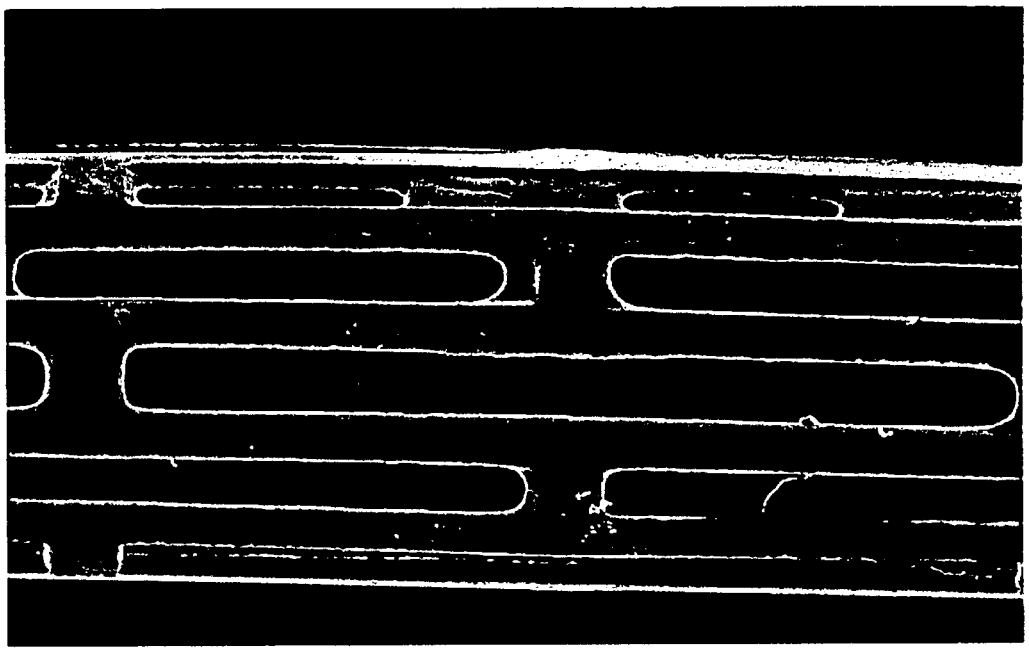

The rapamycin/silicone-coated surface (see 99-05-8071-67-3 in FIG. 9) has particles distributed over it, rather than dissolved into the solution. This result is related to the solvency of the added xylene solvent. Experiments have shown that solvents that can maintain rapamycin in solution (e.g. chloroform, CHCl3) gave a coating surface essentially devoid of these particles (see 99-05-8071-52-2 in FIG. 10). Unfortunately, these solvents did not have the slow evaporation rate required for this process.

Figure 11:
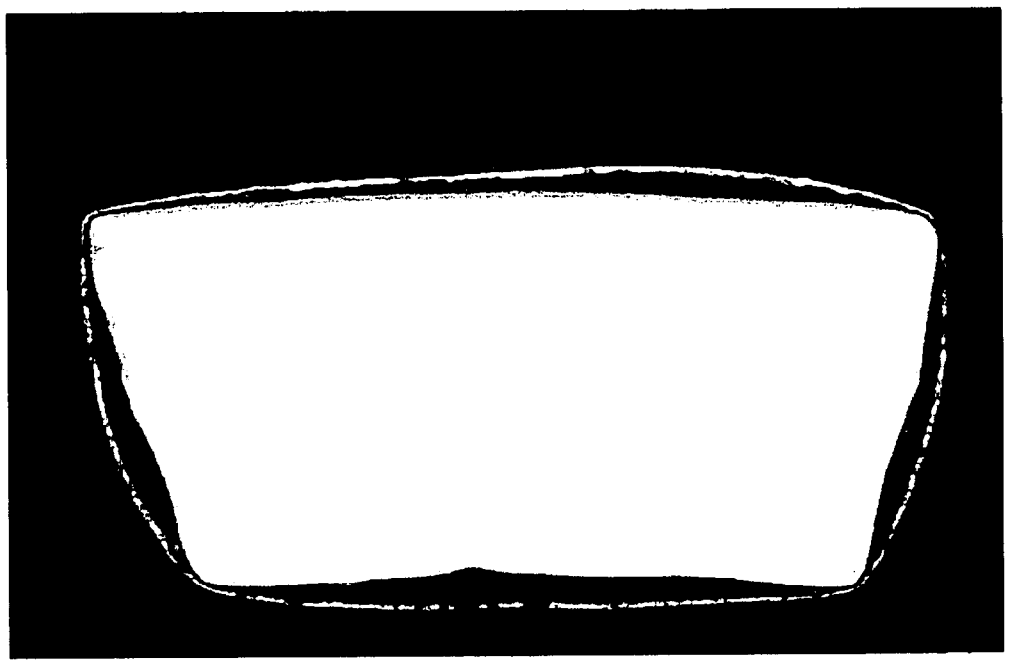

The coating thickness for the 99-05-8071-67-3 stent was about 1 to 8 $\mu$m (see FIG. 11).

EXAMPLE 8

Four cured, coated stent samples were then analyzed for volatility, as described below:

| Stent # | Description |
|---|---|
| 99-058071-67-2 | With Rapamycin, cured 18 hours @ 35° C. in a saturated water atmosphere. |
| 99-058071-67-9 | Without Rapamycin, cured 18 hours @ 35° C. in a saturated water atmosphere. |
| 99-058071-67-6 | With Rapamycin, cured 18 hours @ 35° C. in a saturated water atmosphere. Placed under vacuum (−28" Hg) at Room Temperature for about 18 hours. |

-continued

| Stent # | Description |
|---|---|
| 99-058071-68-3 | Without Rapamycin, cured 18 hours @ 35° C. in a saturated water atmosphere. Placed under vacuum (−28" Hg) at Room Temperature for about 18 hours. |

The volatility of each of the stents was quite low; the silicone-only coatings are particularly clean from residuals of 1,1,1-trichloroethane, ethyl benzene, xylene and acetic acid (a residue from the curing process).

EXAMPLE 9

Stent Inflation

It then had to be determined if the stents coated in such a manner would inflate as to nominal dimensions. Inflation was carried out on the following four coated stents:

| Stent # | Description |
|---|---|
| 99-058071-67-1 | Silicone/Rapamycin coating |
| 99-058071-67-5 | Silicone/Rapamycin coating on SP-1 treated stent |
| 99-058071-67-8 | Silicone-only coating |
| 99-058071-68-2 | Silicone-only coating on SP-1 treated stent |

Figure 12:
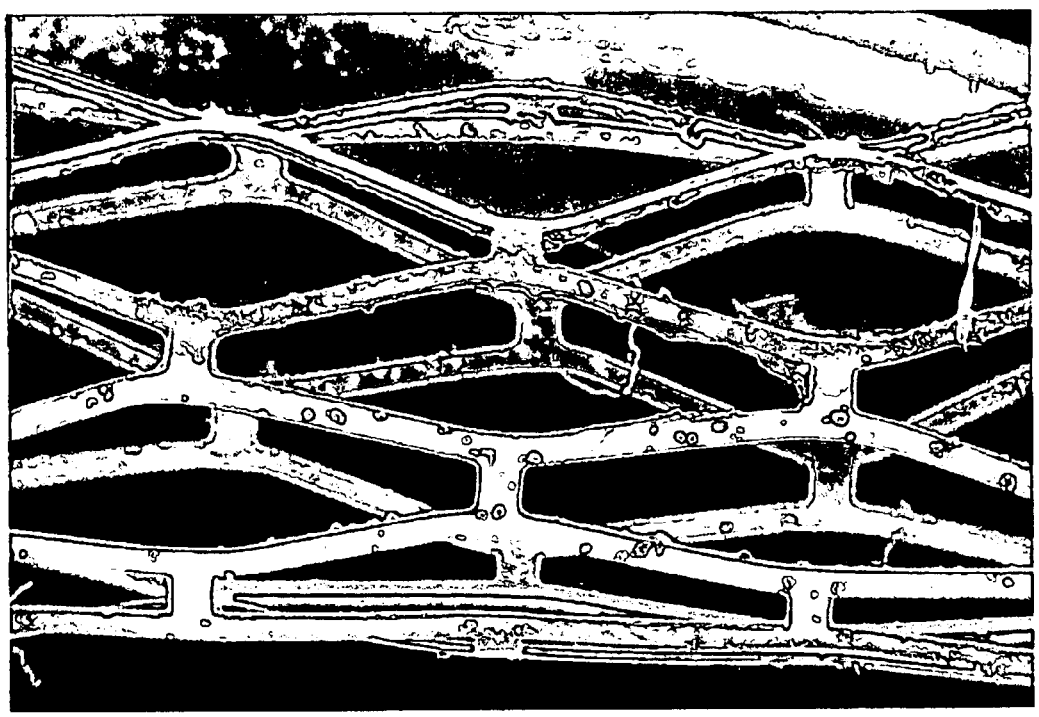
Figure 13:
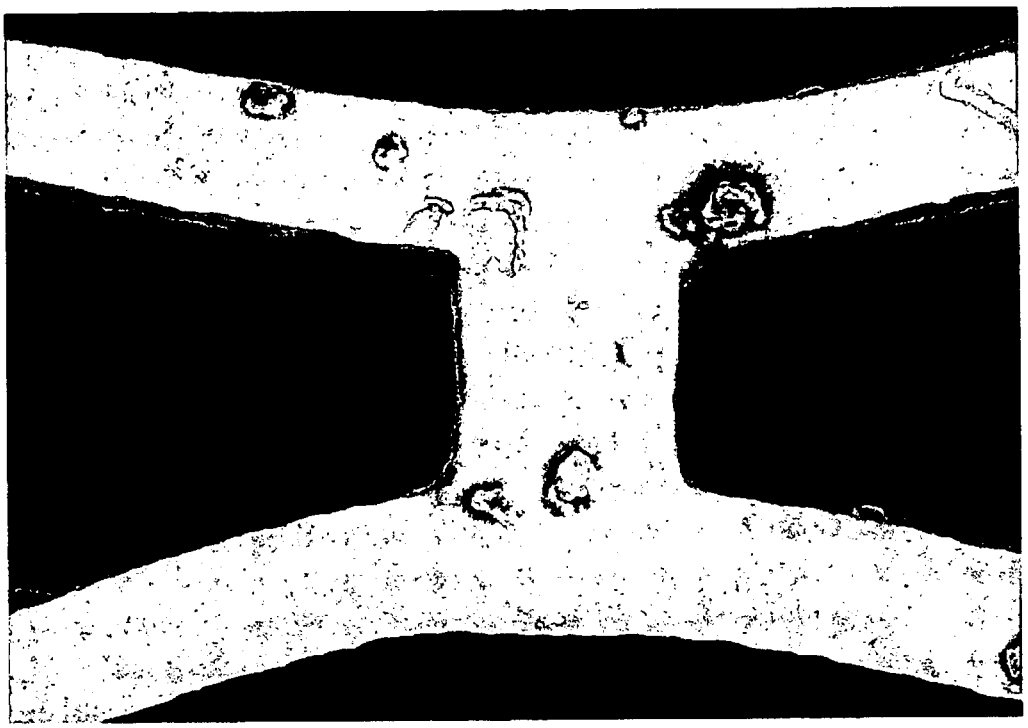
Figure 14:
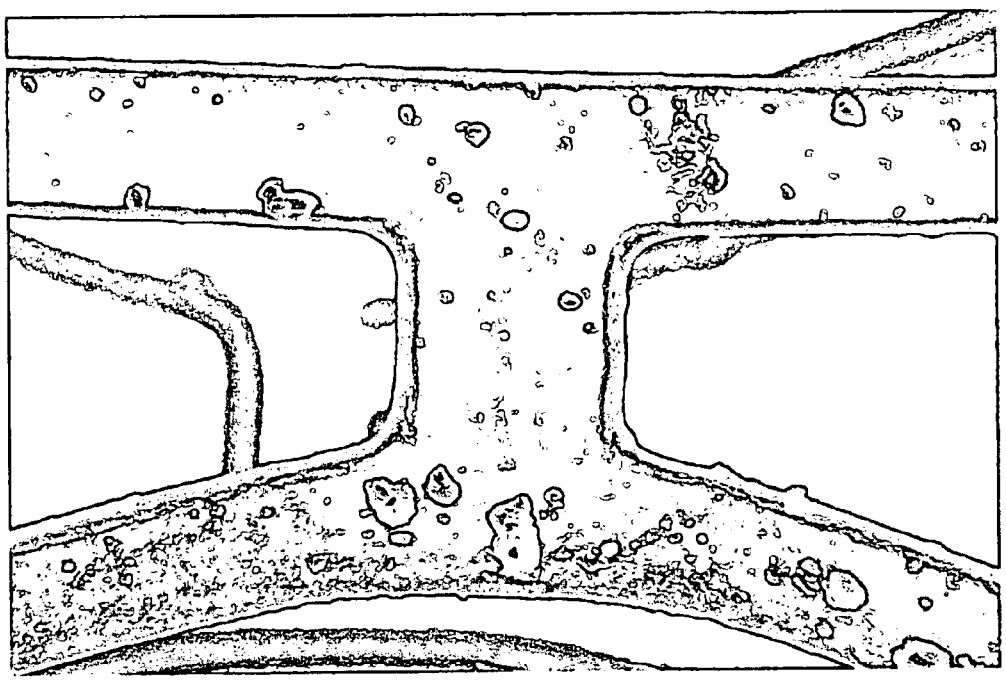

The inflated surface of the 99-058071-67-1 silicone/rapamycin-coated stent is shown in FIG. 12. No obvious cracks are seen where the stent crossover T is seen in FIG. 13. However, there may be some detachment of the film, which might be due to handling damage. It may be that the silicone is relatively poorly bonded to the stainless steel surface. Some improvement comes from using the SP-1 adhesion promoter (see FIG. 14).

Figure 15:
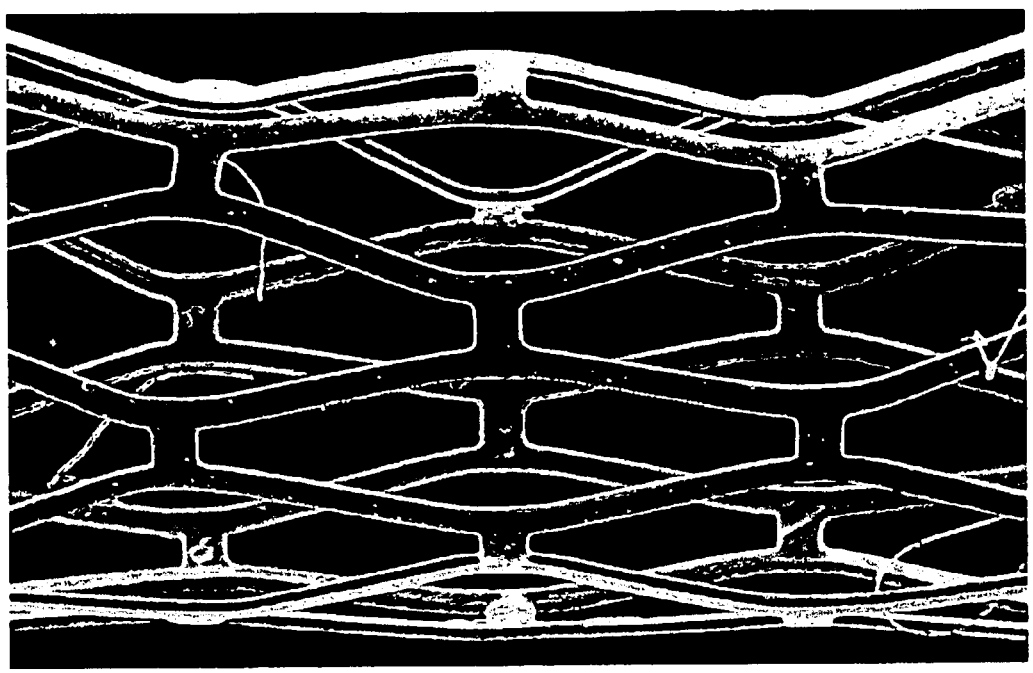
Figure 16:
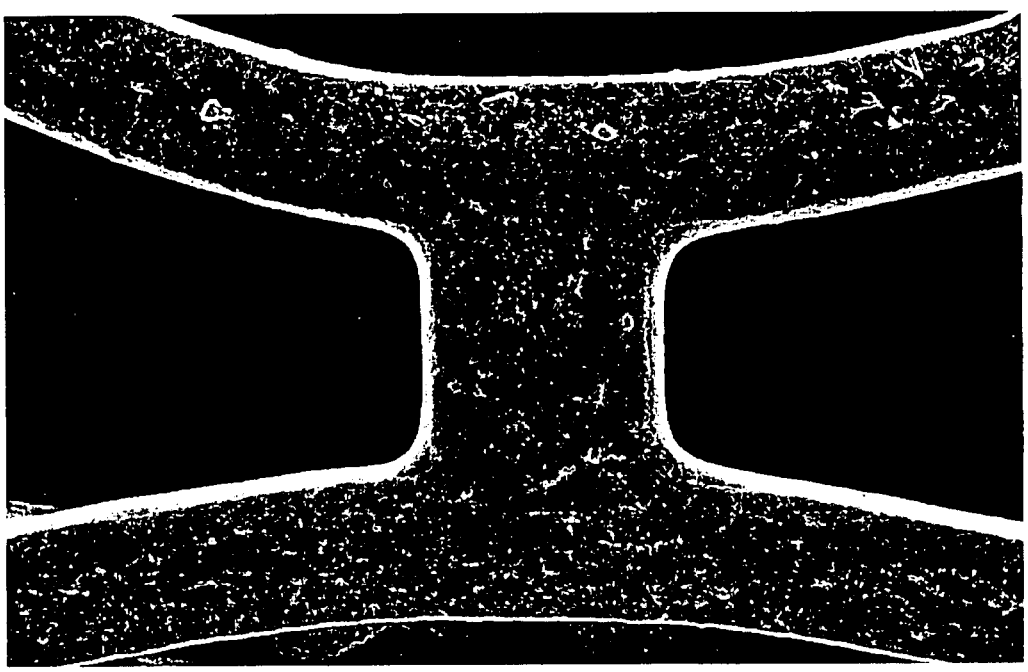

The inflated silicone-only coated 99-058071-67-8 stent is shown in FIGS. 15 and 16. There are no evident cracks or other problems.

Figure 17:
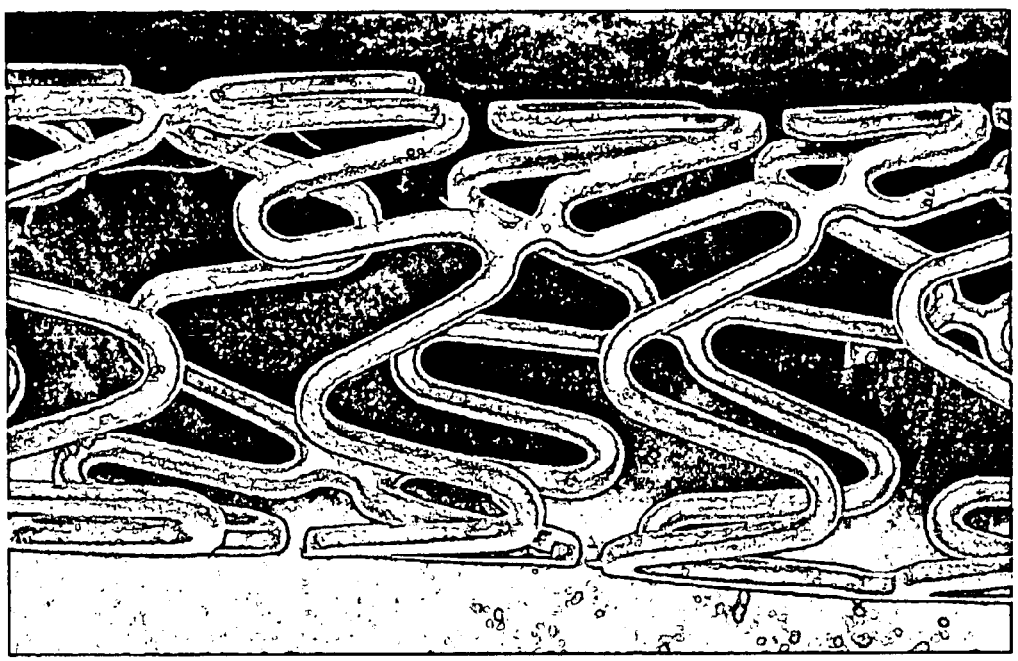
Figure 18:
Figure 19:
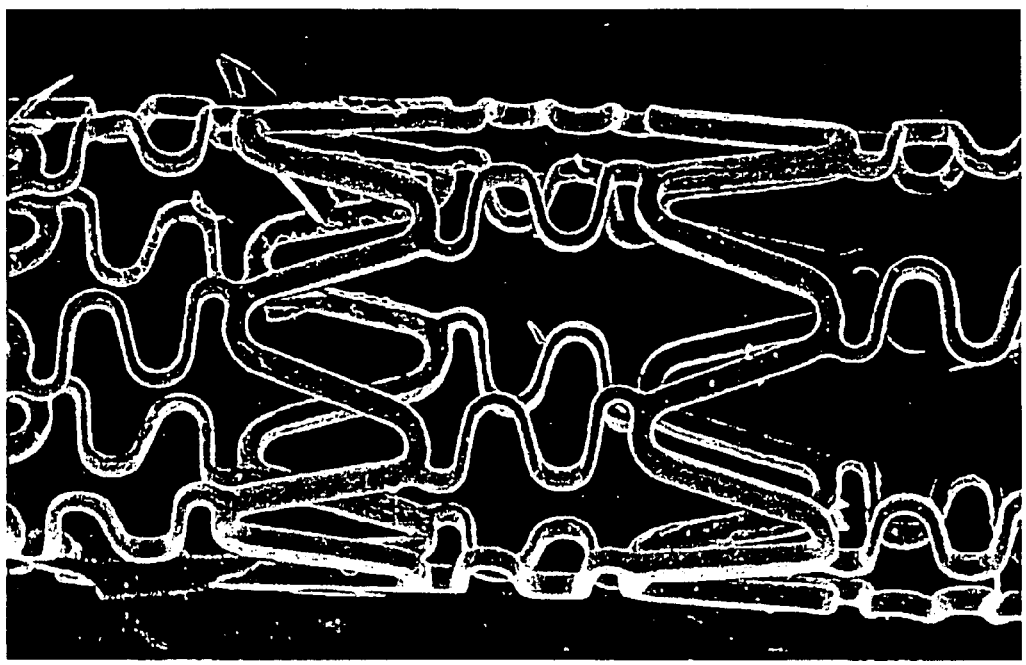
Figure 20:

When the above described processes were used with other stents (Crossflex® and Bx-Velocity® stents, again produced by Cordis), it was found that a 10.9% silicone solution concentration was the highest that could be used without causing blockage in open areas of the stents. SEM photographs of the inflated-coated Crossflex (FIGS. 17 and 18) and BX-Velocity (FIGS. 19 and 20) show that the coating did not crack on inflation.

It is important to realize that the polymer coating used to accomplish the objects of this invention is unimportant, so long as the stent is coated properly with a therapeutic amount of drug which continues to cling to the stent after removal from the mandrel 10. For instance, it has been determined that a copolymer of n-butyl methacrylate and n-hexyl methacrylate with rapamycin contained therein works well as a coating for the Crossflex® stents described above. Similarly, the use of n-butyl methacrylate can be substituted with 2-ethylbutyl methacrylate, again to coat the stent with rapamycin. This mixture also works well. Other combinations are certainly foreseeable too.

The results of the stent coating experiments can be summarized as follows. A simple stent dip, followed by insertion over a mandrel to remove the excess coating solution, did not work well. The solution dried too quickly and in an uncontrolled manner, so that the thickness of solution on the stent varied considerably from stent to stent. A coat, spin, move and dry procedure was the best method. The ability to turn the mandrel to "spin off" the excess drug/polymer solution is an important part of creating an even coat on the stent. The excess solution would otherwise contribute to a thick, uneven coating and blockage of stent slots. Initially done by hand, the process is better served by an apparatus that can turn the mandrel at high speeds in a reproducible manner.

Also, the solvent used in the process must have several properties: It must solvate the polymer (in this case the RTV silicone). The solvent should dry slowly enough that it is possible to form the coat into its final configuration before drying changes its viscosity appreciably. Also, the solvent should solvate the drug, to avoid particulates forming on the stent surface. From the foregoing examples, we see that xylene acts as a suitable solvent for the silicone polymer and had a relatively slow evaporation rate, but rapamycin was not soluble in it.

The solution viscosity is important to facilitate flow in "spin-off" and re-arrangement of the film to an even coating. Viscosity is dependent on solids type/concentration and solvent type. As the solution dries, its viscosity rises, making it more difficult for the solution to move or be spun off (hence the requirement for slow drying solvents in the coating mix). Silicone solids in the range of 10% to 16% in solution was determined to result in coating thickness within the range of the desired 10 $\mu$m. Higher percentage solid coatings would give thicker coatings, but with increased likelihood of blockage of stent slots.

The size of the mandrel 10 is important. It should be thick enough in diameter to prevent excessive retention of solution but small enough that the stent does not stick to the mandrel during stent removal. The stent is placed at one end of the mandrel and slowly moved forward in a series of steps, each of which slowly whittles down the interior layer thickness. In this work, a 1.27-mm diameter mandrel gave good results with a 1.5-mm inner diameter stent.

EXAMPLE 10

The Process in Recapitulation

In recapitulation, the process is as follows:

Cleaning of Stents
 1. Put stents to be cleaned in a 100-ml beaker and add about 20 ml of reagent grade dichloromethane (DCM) solvent.
 2. Cover solution with a watch glass.
 3. Sonicate the stent/solvent beaker for about 1 minute.
 4. Leave stents in DCM until use.

Preparation of Stent on Mandrel
 5. Clean 1.27 mm diameter mandrel by wiping with a Kimwipe®, soaked with acetone. Set aside to dry on a clean surface.

Setting up for Coating Run
 6. Place stent on mandrel by using end of mandrel to insert into one end of the stent and slowly pushing onto the mandrel from the DCM solution.
 7. By tapping the mandrel from the opposite end, allow the stent to slide over the mandrel to the opposite end of the mandrel. You can also use a scalpel to slowly push the stent down; it should move freely.
 8. Insert mandrel into mandrel chuck on apparatus.
 9. Once on the apparatus, turn on the mandrel motor and rotate at high speed for a few seconds while blowing the stent with dry, clean nitrogen gas. This serves to dry off the stent of any residual DCM solvent Preparation of Coating Solution 10. Weigh out, to 5 decimal places, the silicone polymer solution into a 2-ml vial.
11. Weigh out the rapamycin drug (if required) and put into vial.
12. Add solvent (e.g. xylene) to vial. Record weights of all components.
13. Seal the vial with a screw top (note: vial top should be compatible with the solvents in use) and then shake up the vial to mix the components. Sonicate the mixture for about 5 minutes.

Preparation of Coated Stent

14. Using a plastic 1 ml syringe, transfer a small amount (about 0.5 ml) of the solution onto the stent by dropping the solution over the stent on the mandrel. Be sure to thoroughly coat the stent.
15. Immediately turn on the mandrel motor and rotate at 4000 RPM. This serves to throw off any excess solution from the stent and provide the proper distribution of the solution on the stent surface. Use the push button to turn the motor on and off in pulses of about 1 sec. This process serves to constantly accelerate/decelerate the stent and keeps it moving relative to the mandrel to avoid sticking.
16. After about 15 seconds, turn off the motor and move the stent about one stent length down the mandrel onto a clean section. This step is commonly known as "indexing" the stent. Again turn on the mandrel motor and pulse the motor for about 10 seconds. Repeat this step 16 two (or more) times.
17. Turn off the motor and move the stent about 2 stent lengths down the mandrel to a clean section. Turn the motor to full speed while blowing the stent with clean, dry nitrogen for about 20 seconds.
18. Turn off the motor, and slowly move the stent forward using a scalpel or other instrument, and push off into a receiving vial.
19. Remove the mandrel from the apparatus, clean, and prepare for the next run.

Coating Cure

20. The polymer is an RTV silicone, which means that it cures at room temperature in about 24 hours. Moisture is required for the cure. Therefore, place the sample in a very moist environment for 1 day. One easy way to do this is to use a forced air oven and place a container of water at the bottom of the oven. Maintain the oven temperate at ambient or slightly above. The forced air will pick up the moisture by evaporation from the container and cure the polymer on the stent.

What is claimed is:

1. A process for coating stents with a coating, comprising:
    placing a stent on a mandrel;
    transferring an amount of a coating solution onto the surface of said stent;
    rotating said mandrel;
    indexing said stent along said mandrel;
    rotating said mandrel;
    removing said stent from said mandrel, and
    wherein said rotating steps include rotating said mandrel in a series of pulses; and wherein said process further comprises an additional step of indexing said stent about two stent lengths along said mandrel, and then rotating said mandrel, said additional step accomplished prior to removing said stent.
2. The process of claim 1 wherein the first of said indexing steps comprises moving said stent about one stent length along said mandrel.
3. The process of claim 1 wherein the coating comprises a polymer and a drug.
4. The process of claim 3 wherein the polymer is a silicone.
5. The process of claim 3 wherein the drug is rapamycin.
6. The process of claim 1 wherein the amount of said solution placed onto said stent is about 0.5 ml.
7. The process of claim 1 wherein said pulses are of about 1 second duration.
8. A process for coating stents with a coating, comprising:
    placing a stent on a mandrel;
    transferring an amount of a coating solution onto the surface of said stent;
    rotating said mandrel;
    indexing said stent along said mandrel;
    rotating said mandrel;
    removing said stent from said mandrel; and
    wherein said rotating steps include rotating said mandrel at a rate in excess of about 4000-rpm; and
    wherein said process further comprises an additional step of indexing said stent about two stent lengths along said mandrel, and then rotating said mandrel, said additional step accomplished prior to removing said stent.
9. The process of claim 8 wherein the coating comprises a polymer and a drug.
10. The process of claim 9 wherein the polymer is a silicone.
11. The process of claim 9 wherein the drug is rapamycin.
12. The process of claim 8 wherein the amount of said solution placed onto said stent is about 0.5 ml.

* * * * *